United States Patent
Watkins et al.

(10) Patent No.: US 6,618,608 B1
(45) Date of Patent: Sep. 9, 2003

(54) THERMAL IMAGING OF FAT AND MUSCLE USING A SIMULTANEOUS PHASE AND MAGNITUDE DOUBLE ECHO SEQUENCE

(75) Inventors: Ronald D. Watkins, Niskayuna, NY (US); Harvey E. Cline, Niskayuna, NY (US)

(73) Assignee: Txsonics, Ltd., Tirat Carmel (IL)

( * ) Notice: Subject to any disclaimer, the term of this patent is extended or adjusted under 35 U.S.C. 154(b) by 0 days.

(21) Appl. No.: 09/696,624

(22) Filed: Oct. 24, 2000

Related U.S. Application Data

(60) Provisional application No. 60/168,122, filed on Nov. 30, 1999.

(51) Int. Cl.[7] ................................................. A61B 5/05
(52) U.S. Cl. ...................................................... 600/412
(58) Field of Search ................................. 600/407, 409, 600/410, 412, 437, 438, 549; 324/307, 308, 309, 315

(56) References Cited

U.S. PATENT DOCUMENTS

| | | | | |
|---|---|---|---|---|
| 5,187,439 A | * | 2/1993 | Jensen et al. | 324/309 |
| 5,323,779 A | * | 6/1994 | Hardy et al. | 600/411 |
| 5,594,336 A | * | 1/1997 | Gullapalli et al. | 324/309 |
| 5,633,586 A | * | 5/1997 | Finn | 324/309 |
| 5,916,161 A | * | 6/1999 | Ishihara et al. | 324/315 |
| 6,064,206 A | * | 5/2000 | Van Vaals et al. | 324/309 |
| 6,067,371 A | * | 5/2000 | Gouge et al. | 382/128 |
| 6,377,834 B1 | * | 4/2002 | Zhou et al. | 324/315 |

* cited by examiner

Primary Examiner—Sang Paik
(74) Attorney, Agent, or Firm—Bingham McCutchen LLP

(57) ABSTRACT

A method for magnetic resonance imaging includes applying a first two echo gradient echo sequence to a tissue region, the first two echo sequence generating a first echo and a subsequent second echo. A second two echo gradient echo sequence is applied after heating the tissue region, the second two echo sequence generating a third echo and a subsequent fourth echo. A magnitude difference between the third echo and the first echo is measured and correlated to a temperature shift for fat tissue, and a phase difference between the fourth echo and the second echo is measured and correlated to a temperature shift for water-based tissue. A thermal image is generated of the tissue region based upon the temperature shift for both fat and water-based tissue.

20 Claims, 3 Drawing Sheets

THERMAL IMAGING OF FAT AND MUSCLE USING A SIMULTANEOUS PHASE AND MAGNITUDE DOUBLE ECHO SEQUENCE

This application claims the benefit of U.S. Provisional Application No. 60/168,122, filed Nov. 30, 1999, the disclosure of which is incorporated herein by reference.

FIELD OF THE INVENTION

The present invention relates generally to systems and methods for imaging tissue using magnetic resonance imaging, and more particularly to systems and methods for performing thermal-sensitive imaging of both fat and muscle tissue using focused magnetic resonance imaging.

BACKGROUND

A number of methods have been proposed for directing heat to a target tissue region within a patient, such as a cancerous or benign tumor, to necrose or otherwise treat the tissue region with thermal energy. For example, a piezoelectric transducer located outside the patient's body may be used to focus high intensity acoustic waves, such as ultrasonic waves (acoustic waves with a frequency greater than about twenty kilohertz (20 kHz), and more typically between one and five Megahertz (1–5 MHz)), at an internal tissue region of a patient to therapeutically treat the tissue region. The ultrasonic waves may be used to ablate a tumor, thereby obviating the need for invasive surgery. In an alternative method, laser fibers may be introduced into the patient's body from an entry site that are used to guide coherent optical heat sources to an internal tissue region.

During such procedures, it is often desirable to image the tissues being treated. For example, ultrasound imaging systems may be used for imaging, as well as for generating therapeutic ultrasound waves. Alternatively, magnetic resonance imaging (or "MRI") may be used instead of ultrasound imaging, as MRI provides excellent quality images of tissue, and is not limited to "windows" that exclude bone or other structures that may interfere with or otherwise limit ultrasound imaging.

An MRI system may be used to plan a procedure, for example, before surgery or a minimally invasive procedure, such as an ultrasound ablation procedure. A patient may initially be scanned in an MRI system to locate a target tissue region and/or to plan a trajectory between an entry point and the tissue region in preparation for a procedure. Such preparation may be particularly useful because a tumor may be more visible in an magnetic resonance ("MR") image than using direct examination. Due to differences in relaxation times of tumorous and other tissue, MRI images may provide a contrast not available using direct visualization, particularly since tumorous tissue may visually appear similar to normal tissue, or the field of view may be obscured, for example, by blood.

Once the target tissue region has been identified, MRI may be used during the procedure, for example, to image the tissue region and/or to guide the trajectory of an external ultrasound beam to a target tissue region being treated, or to guide laser energy. In addition, an MRI system may be used to monitor the temperature of the tissue region during the procedure, for example, to ensure that only the target tissue region is necrosed during an ablation procedure without damaging surrounding healthy tissue. Generally, this involves using a separate scanning sequence that provides temperature information, in addition, to a scanning sequence that provides tissue information.

For example, before applying sufficient energy to necrose tissue, a lower level of energy may be directed towards the target tissue region, generally in a pulsed or oscillating manner to minimize the effect of thermal diffusion. As the tissue region is heated, a temperature-sensitive magnetic resonance ("MR") pulse sequence may be used to acquire a temperature "map" to ensure that the energy is applied to the target tissue region and not to the surrounding healthy tissue. The imaging system may also be used in a separate scan sequence to create an image of the tissue intended to be destroyed, and then the two images may be superimposed upon one another to identify the location of the energy relative to the target tissue region.

The placement of the energy may then be adjusted to direct the energy more accurately towards the target tissue region. For example, a focal zone of ultrasonic energy emitted by an ultrasound transducer may be moved by mechanically adjusting the position of the transducer relative to the patient's body. Alternatively, the focal zone may be moved electronically. e.g., by controlling a phase component and/or relative amplitude of drive signals to the transducer elements, or a combination of mechanical and electronic positioning may be used, as is known in the art.

MRI systems exploit the property that free unpaired spinning protons in the nucleus of a molecule of a specific tissue, such as hydrogen molecules, align themselves in a magnetic field such that their axes precess about the magnetic field. Such unpaired protons have non-zero "spin" and consequently behave like a small magnetic dipole. The net sum of the population of dipoles results in a bulk magnetization vector M that is aligned with a static magnetic field $B_0$, shown in FIG. 1 in a reference frame X'Y'Z', and rotating about the static magnetic field axis at a frequency equal to the precession of the spins (the Larmor frequency).

The magnetic dipoles forming the net magnetization vector M ordinarily are aligned with the applied magnetic field. However, these magnetic dipoles have an excited state that opposes this applied magnetic field. Pulses resulting from an RF excitation at the Larmor frequency will cause the magnetic dipoles to transition from the aligned state to the opposing state. An MR imaging device uses a radio frequency (RF) transmitter to "flip" the magnetic dipoles into the excited state by transmitting RF energy at the Larmor frequency. For example, a one hundred eight degree (180°) pulse from the RF transmitter will rotate or "flip" the magnetization vector M down to align along the –Z' axis. This behavior is generic to any orientation of the magnetization vector.

Regardless of the flip angle excited by the RF transmitter, it is possible, by applying a magnetic field gradient, to selectively choose spins for excitation. This selection is necessary for imaging of a tissue structure. A one-dimensional linear magnetic field gradient, conventionally denoted in the Z direction, is applied during the RF excitation pulse. Because of the linear gradient, only spins located in a particular slice or plane through the patient will respond to a given RF pulse.

FIG. 2 illustrates the resulting net magnetization vector M after application of a ninety degree (90°) pulse. This vector aligns with the $Y_2$ axis and thus is entirely in the transverse X'Y' plane. Two time constants, $T_1$ and $T_2$, govern the relaxation of this perturbed or excited magnetic field vector back to the equilibrium state of FIG. 1. $T_1$ relates to the time necessary for the decay in the longitudinal component of the excited magnetization vector. $T_2$ relates to the time necessary for the decay in the transverse component of the excited magnetization vector. Because two factors contribute to the decay of transverse magnetization, a combined time constant $T_2^*$ is generally used to represent the two contributions.

One commonly used pulse sequence in MRI systems is known as a spin-echo sequence. In its traditional form, a ninety degree (90°) RF pulse is first applied to the spins, as discussed with respect to FIG. 2. Because the spins are all in slightly different environments, the transverse magnetic field begins to dephase. During this dephasing period, a one hundred eighty degree (180°) pulse is applied. This pulse causes the transverse magnetic field to partially rephase such that a signal is produced called an echo, which is a function of both time constants $T_1$ and $T_2^*$. Alternatively, other sequences may be used, such as a gradient echo sequence, a gradient refocused echo sequence, as are well known to those skilled in the art.

To image the spins within the slice created by the slice or Z-axis gradient discussed earlier, two additional gradients are typically applied. The first gradient, called the phase encoding gradient, is applied along one of the sides of the image plane, i.e., conventionally denoted to be on the Y-axis (phase encode axis). Once the phase encoding gradient is turned off, the second gradient, called the frequency encoding gradient, is applied along the remaining edge of the image plane, conventionally denoted to be on the X-axis (readout axis).

Specific thermal imaging pulse sequences have been developed for imaging temperature characteristics within tissue. These sequences have generally used either the temperature sensitivity of the $T_1$ relaxation process, diffusivity contrast, or the shift in the proton resonance peak with respect to temperature. There is interest in applying MRI-guided focused ultrasound to ablate tumors in tissues, such as breast tissue, which contain considerable amounts of fat overlying the pectoral muscle.

Accordingly, it would be desirable to provide systems and methods for imaging a body region containing water-based tissue, such as muscle, as well as fat tissue, using an MR imaging system.

SUMMARY OF THE INVENTION

The present invention is directed to systems and methods for imaging tissue using magnetic resonance imaging, and more particularly to methods for performing thermal-sensitive imaging of both fat and muscle tissue using focused magnetic resonance imaging.

In accordance with one aspect of the present invention, a method for thermal magnetic resonance imaging is provided that includes generating a first two echo gradient echo sequence before heating a tissue region within a patient, the first two echo sequence having a first echo optimized for temperature contrast in amplitude from fat tissue and a second echo optimized for temperature phase contrast from water-based tissue. A second two echo gradient echo sequence is generated after heating the tissue region, the second double echo sequence having a third echo optimized for temperature contrast in amplitude from fat tissue and a fourth echo optimized for temperature phase contrast from water-based tissue. Thus, a single RF excitation pulse during each of the two echo sequences may be used to generate the respective pairs of echoes.

The first echo is compared to the third echo to obtain a temperature shift representative of fat tissue, and the second echo is compared to the fourth echo to obtain a temperature shift representative of water-based tissue. In a preferred embodiment, a magnitude difference between the third echo and the first echo is measured and correlated to the temperature shift in fat tissue, and a phase difference between the fourth echo and the second echo is measured and correlated to the temperature shift in water-based tissue. A thermal image may then be generated of the tissue region based upon the temperature shifts in fat and water-based tissue.

In accordance with another aspect of the present invention, a method for thermal magnetic resonance imaging is provided that includes generating a first 'two echo gradient echo sequence before heating a tissue region within a patient, the first two echo sequence having a first echo optimized for temperature contrast from fat tissue and a second echo optimized for temperature contrast from water-based tissue. Thermal energy is directed towards the tissue region, for example, using a focused ultrasound system. A second two echo sequence is then generated, the second two echo sequence having a third echo optimized for temperature contrast from fat tissue and a fourth echo optimized for temperature contrast from water-based tissue.

The third echo and the first echo may be compared to obtain a first difference, and the fourth echo and the second echo may be compared to obtain a second difference. A complex difference of the first and second differences may then be combined to facilitate identifying a location of the thermal energy. Alternatively, the complex difference may be compared with at least one of the first difference and the second difference to identify whether the location of the thermal energy is within fat tissue or muscle tissue.

In accordance with yet another aspect of the present invention, a method for thermal magnetic resonance imaging is provided that includes applying a first two echo gradient echo sequence to a tissue region of a patient, the first two echo sequence generating a first echo and a subsequent second echo within the tissue region. Thermal energy is directed towards the tissue region, for example, using a focused ultrasound system. A second two echo gradient echo sequence is applied after directing the thermal energy towards the tissue region, the second two echo sequence generating a third echo and a subsequent fourth echo within the tissue region.

The first echo is compared to the third echo to obtain temperature shift data for fat tissue within the tissue region, and the second echo is compared to the fourth echo to obtain temperature shift data for water-based tissue within the tissue region. Preferably, a magnitude difference between the third echo and the first echo is measured that may be correlated to the temperature shift for fat tissue, and a phase difference between the fourth echo and the second echo is measured that may be correlated to the temperature shift for water-based tissue.

A thermal image may then be generated of the tissue region based upon the temperature shift data for both fat and water-based tissue. Alternatively, a complex difference between the temperature shift data for the fat tissue and the water-based tissue may be combined to identify a location of the thermal energy. Thus, the present invention may provide systems and methods that facilitate monitoring a target tissue region, such as tumor, being treated to ensure that the target tissue region is necrosed without damaging surrounding healthy tissue.

Other objects and features of the present invention will become apparent from consideration of the following description taken in conjunction with the accompanying drawings.

BRIEF DESCRIPTION OF THE DRAWINGS

Preferred embodiments of the present invention are illustrated by way of example, and not by way of limitation, in the figures of the accompanying drawings, in which like reference numerals refer to like components, and in which.

DETAILED DESCRIPTION OF THE PREFERRED EMBODIMENTS

Figure 1:
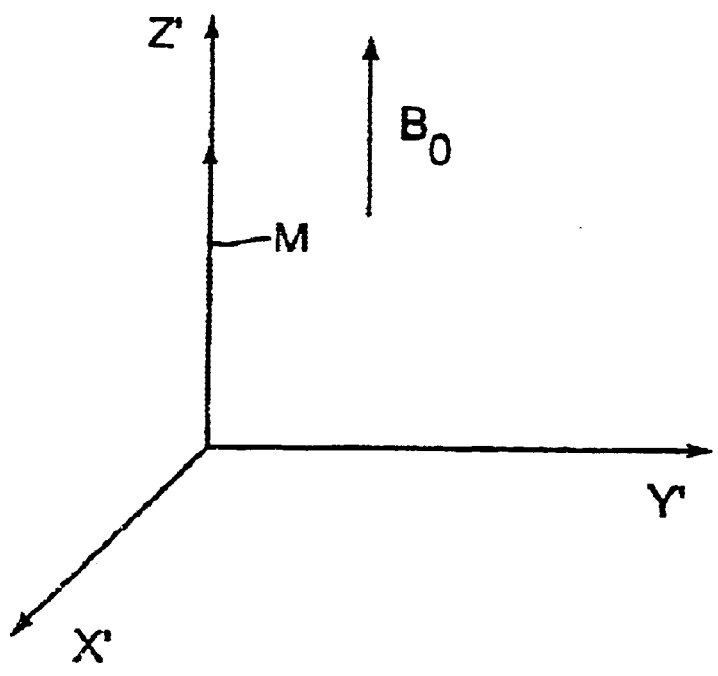
FIG. 1 is a representation of a bulk magnetization vector M, arising from unpaired resonant nuclei (spins) within the tissue of a patient in a static magnetic field, shown in a reference frame X'Y'Z' rotating about the static magnetic field equal to the precession frequency of the spins.
Figure 2:
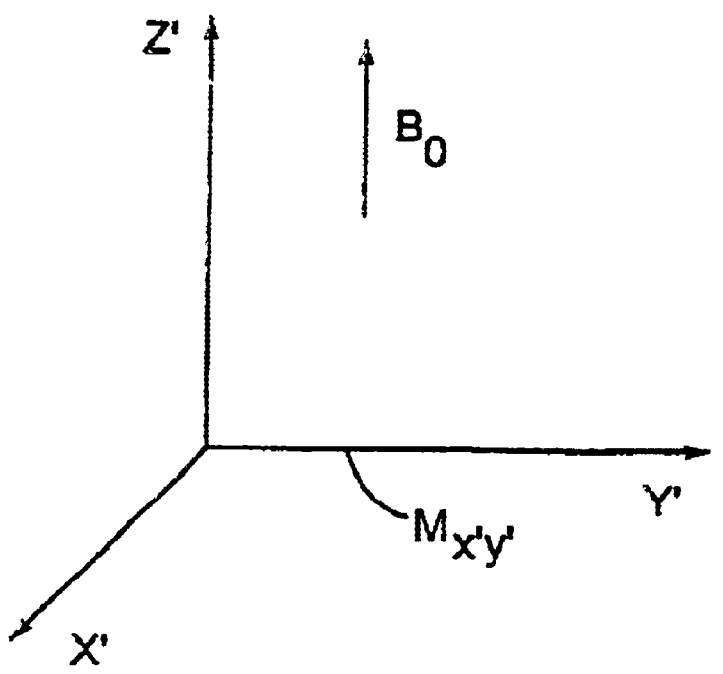
FIG. 2 is a representation of the bulk magnetization vector M of FIG. 1, also in reference frame X'Y'Z', after an RF excitation pulse is applied to tip it into the transverse plane X'Y'.
Figure 3:
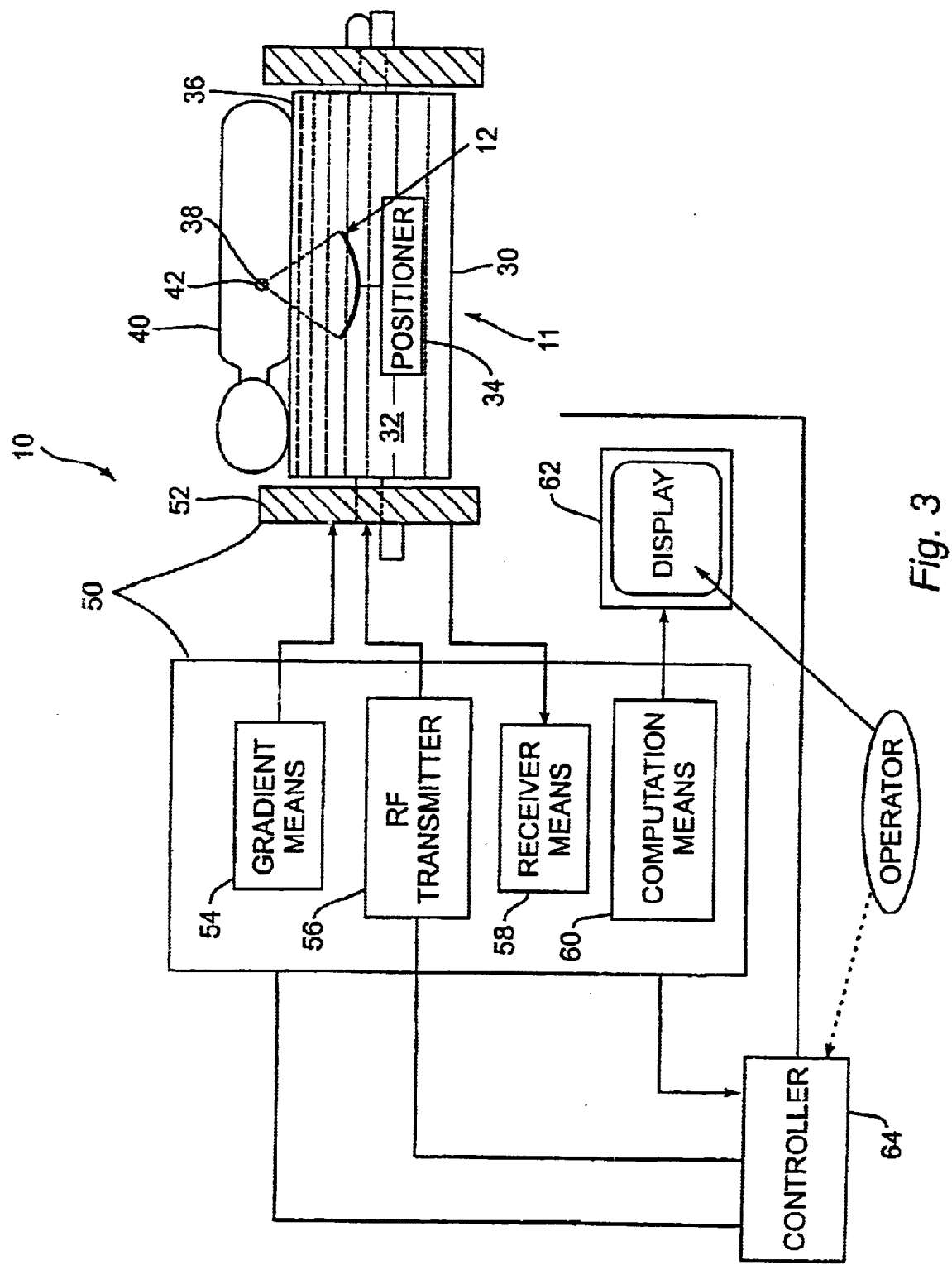
FIG. 3 is a schematic diagram of a focused ultrasound system including a MR imaging system, in accordance with the present invention.

Turning now to the drawings, FIG. 3 shows a schematic block diagram of an MRI-guided ultrasound pulsed heat system 10, in accordance with one aspect of the present invention. The system 10 generally includes a focused ultrasound system 11, and a magnetic resonance imaging ("MRI") system 50. In alternative embodiments, other systems for delivering thermal energy to a target tissue region may be provided instead of a focused ultrasound system, such as coherent optical heat sources that may be guided by laser fiber, and the like.

The focused ultrasound system 11 includes a piezoelectric transducer 12, which is preferably mounted within a chamber 32 filled with degassed water or similar acoustically transmitting fluid. The chamber 32 may be located within a table 30 upon which a patient 40 may be disposed or within a fluid-filled bag mounted on a movable arm that may be placed against a patient's body (not shown). The transducer is coupled to drive circuitry and/or a controller (not shown) for generating and/or controlling the ultrasonic energy emitted by the transducer, as is well known in the art.

In a preferred embodiment, the transducer 12 is a spherical cap transducer array that is divided into a plurality of concentric rings and/or angular sectors (not shown). The configuration of the transducer 12, however, is not important to the present invention, and any of a variety of known ultrasound transducers may be used, such as flat circular arrays, linear arrays, and the like. A positioning system 34 may be connected to the transducer 12 for mechanically moving the transducer 12 in one or more directions, and preferably in any of three orthogonal directions. Alternatively, a focal distance (a distance from the transducer 12 to a focal zone 38 of the ultrasonic energy emitted by the transducer 12) may be electronically adjusted using known methods, or a combination of mechanical and electronic positioning may be used. Exemplary transducers and positioning systems are disclosed in applications Ser. Nos. 09/556,095, filed Apr. 21, 2000, and 09/557,078, filed Apr. 21, 2000. The disclosures of these references and any others cited therein are expressly incorporated herein by reference.

The top of the table 30 generally includes a flexible membrane 36 that is substantially transparent to ultrasound, such as mylar, polyvinyl chloride (PVC), or other suitable plastic material. A fluid-filled bag (not shown) may be provided on the membrane 36 that may conform easily to the contours of the patient 40 disposed on the table 30, thereby acoustically coupling the patient 40 to the transducer 12 within the chamber 32.

The MRI system 50 includes a static field magnet 52, a gradient field amplifier 54, a radio frequency ("RF") transmitter 56, a receiver 58, and a computation unit 60 that may acquire images of the tissue structure 42. The magnet 52 includes a region for receiving a patient therein, and provides a static, relatively homogeneous magnetic field $B_0$ over the patient 40, as is well known in the art. Gradient field amplifier 54 generates magnetic field gradients that vary the static magnetic field $B_0$ in a known manner, and/or as described further below.

The RF transmitter 56 generates and transmits the necessary RF pulse sequences over the patient 40 to cause the tissue structure 42 to emit MR response signals, which may include free induction decay (FID) signals and/or echo signals. In a preferred embodiment, the RF transmitter 56 includes RF coils (not shown) in the magnet 52, and a pulse transmitter (also not shown), which may have a pulse transmitter frequency supplied by a synthesizer and/or may be controlled by a control processor (both also not shown).

Raw MR response signals may.be sensed by the receiver 58, which may include a separate set of RF coils (not shown) from the RF transmitter 50. Alternatively, the RF transmitter 56 may be configured to operate alternately in a transmitting mode and then in a receiving mode to receive the MR response signals, for example, by switching the RF coils of the RF transmitter 56 using the control processor. The MR response signals may then be passed to the computation unit 60, which may include an analog-to-digital converter and an image processor (both not shown), that computes an MR image. The computation unit 60 may then display the MR images on a display 62.

A controller 64 may be coupled to the MRI system 50 for receiving the MR images from the computation unit 60. The controller 64 may then be used to compute a path from the transducer 12 to the tissue structure 42 and/or control the transducer 12. For example, the controller 64 may actuate the positioning system 34, or otherwise direct the electronics associated with the transducer 12 in order to position the focal zone 38 of the transducer 12 at a desired location, i.e., within the target tissue region 42.

The MRI system 10 employs real-time temperature-sensitive pulse sequences to rapidly acquire temperature-sensitive images of the patient 40. Optionally, these thermal images may be superimposed on another medical diagnostic image (such as a conventional MR image). Since both the tissue structure 42 and heated regions may be imaged, the operator may accurately position the heated region, i.e., the focal zone 38, to correspond to a desired internal structure and accurately heat the target tissue region 42.

Figure 4:
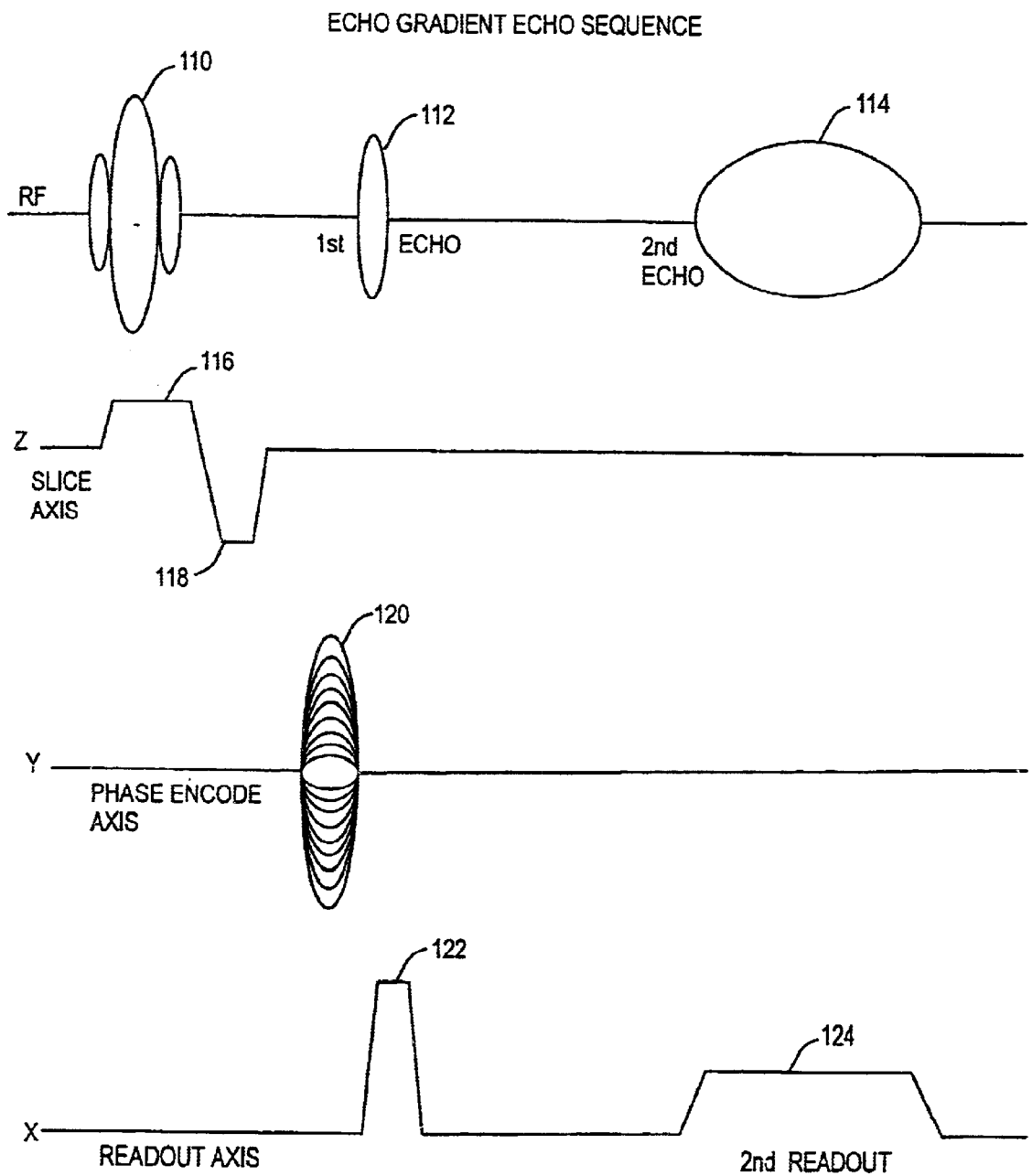
FIG. 4 is a set of graphs showing a two echo gradient echo sequence that may be used to thermally image both fat and muscle tissue, in accordance with the present invention.

Turning to FIG. 4, the MRI system 40 is configured for generating a two echo gradient echo sequence, as shown, that may be used to provide a thermal image of both fat and water-based tissue (i.e., non-fat tissue, such as muscle) using a single RF excitation. The system 40 generally combines information from a relatively fast or "short" echo and a relatively long echo to obtain temperature shift data for fat and muscle tissue, respectively. The temperature shift data of the fat and muscle tissue may then be combined to provide a thermal image of an imaged tissue region. If desired, the thermal image may then be combined with another tissue image, as explained above.

A single RF excitation pulse 110 is used to generate both echoes, preferably causing a relatively low-angle flip, e.g., between about ten and ninety degrees (10–90°). Generally, the preferred flip angle for temperature imaging of water-based tissue, such as muscle, is between about twenty to thirty degrees (20–30°), because of the relatively long $T_1$ of water-based tissue (approximately 800 milliseconds (ms)). Fat tissue, in contrast, has a relatively short $T_1$ (approximately 300 ms), and therefore a higher flip angle, e.g., between about seventy to eighty degrees (70–8°), may be preferred to provide better temperature contrast for fat tissue. Such higher flip angles, however, may cause saturation effects in water-based tissue, and therefore flip angles of between about sixty to seventy degrees (60–70°) are most preferred.

A slice selection gradient 116, 118 is applied with the RF pulse 110, as is well known in the art. A phase encoding gradient 120 is then applied next, along with a dephasing frequency encoding gradient 122 so as to cause the spins to be in phase at the center of the acquisition period. The dephasing frequency encoding gradient is negative in sign from that of the frequency encoding gradient turned on during the acquisition of the MR response signals. Echoes are produced when the frequency encoding gradient is turned on because this gradient refocuses the dephasing that occurs from the dephasing gradient.

The first echo 112, occurring at time $TE_1$, (preferably between about four to five milliseconds (4–5 ms)), may be acquired to provide information attributable to fat tissue. The first echo 112 may be assumed to be produced substantially by fat tissue, because of the relatively short $T_2^*$ of fat tissue, and the relative brightness of MR response signals produced by fat tissue as compared to water-based tissue. By time $TE_2$ (preferably between about ten to twenty milliseconds (10–20 ms)), i.e., the time of the second echo 114, the second echo 114 may be attributable to water-based tissue. Because of the relatively fast $T_2^*$ decay of fat tissue, the signal from fat tissue becomes negligible, and the signal from water-based tissue dominates the second echo 114. By comparing a two echo sequence before and after heating, the MRI system 40 may determine the temperature shift or increase resulting from delivering thermal energy within a target tissue region.

In an alternative embodiment, a gradient refocused echo ("GRE") sequence or other known sequences may be used instead of a gradient echo sequence, as will be appreciated by those skilled in the art. Gradient echo sequences are preferred, however, because the imaging time using gradient echo sequences is generally faster. This is due to the echo times obtained using gradient echo sequences being substantially shorter as compared to those obtained using spin-echo sequences. The magnetization vector M may recover to its equilibrium position along the Z axis more quickly, and therefore allow the imaging sequence to be repeated more rapidly (full recovery being desired before repeating the sequence in order to maximize signal strength). Using gradient echo sequences, however, may result in less signal being available, because the magnetization vector M may recover to equilibrium much more rapidly, and therefore signal strength may be traded off in exchange for a gain in imaging time.

For water-based tissue, the temperature shift calculation is given by the following equation:

$$\Delta T = 2\pi\phi(8\times 10^{-9})F/TE \quad \text{Eq. 1}$$

where the temperature rise $\Delta T$ for the proton resonance shift image depends on the phase shift $\phi$ (radians), the resonance frequency F, the echo time TE, and a coefficient 0.008 ppm/deg C.

Each echo has a magnitude and a phase that may be represented by a complex number or phasor. The second echo 114, which is used to measure the temperature increase in muscle, may thus be represented by $I_C$, the cold complex data (before heating), and by $I_H$, the hot complex data (after heating). To find the phase shift, the complex hot data $I_H$ may be multiplied by the complex conjugate of the cold data $I_C^*$ to give the expression:

$$I_H I_C^* = P_H P_C \exp(i\phi) \quad \text{Eq. 2}$$

where $P_H$ and $P_C$ are the magnitudes of $I_H$ and $I_C$, respectively, i is the square root of –1, and $\phi$ is the phase shift discussed with respect to Eq. 1. By using the expression $\exp(i\phi) = \cos(\phi) + i\sin(\phi)$, the following equations may be derived to solve for the phase shift:

$$\phi = \arctan[Im(I_H I_C^*)/Re(I_H I_C^*)] \quad \text{Eq. 3}$$

$$\phi = \arctan([Re\, I_C Im\, I_H - Re\, I_H Im\, I_C]/[Re\, I_C Re\, I_H + Im\, I_H Im\, I_C])$$

By solving for $\phi$ using Eq. 3 and plugging this value into Eq. 1, the temperature shift in muscle may be determined.

In fat tissue, however, the temperature shift is generally determined empirically, as will be appreciated by those skilled in the art. Within animal tissue, for example, it has been found that the temperature shift is given by about one percent (1%) of the magnitude signal per degree Celsius. Because the fat signal is more intense or "bright" than the muscle signal in the first echo 112 by approximately a factor of two, a magnitude shift method may be used for measuring the temperature shift in fat tissue.

Thus, four images are acquired that may be used to obtain two thermal images. The magnitude difference between the first respective echoes before and after heating may be correlated to a temperature shift in fat tissue, while the phase difference between the second respective echoes before and after heating may be correlated to a temperature shift in muscle tissue. This temperature shift data may then be processed and displayed together to show the temperature contrast of the tissue region being treated.

In an alternative embodiment, the MRI system 40 may measure the magnitude of the complex difference for each echo and combine these difference signals to provide a qualitative indication of the temperature shift, e.g., to identify the focal zone or the region where tissue is being heated, but not necessarily providing an absolute value for the temperature shift. The phase difference for fat is substantially zero and does not contribute to this calculation. The complex difference, Df, for the fat signal in the first echo may simply be the magnitude difference:

$$Df = I_H\text{fat} - I_C\text{fat} \quad \text{Eq. 4}$$

where $I_H$fat and $I_C$fat are the raw complex signal from the first echo after and before heating, respectively. For the second echo, the phase difference for muscle combines with the magnitude difference in estimating the complex difference, Dm:

$$Dm = |I_H - I_C| \quad \text{Eq. 5}$$

$$Dm = Sqrt[I_H^2 + I_C^2 - 2|I_H||I_C|\cos\phi]$$

Note that the contribution from fat in the second echo is very small and may be neglected, as explained above. The signals from the first echo, Eq. [4], and the second echo, Eq. [5] may be combined to form a signal S roughly related to temperature:

$$S = Sqrt(Dm^2 + Df^2) \quad \text{Eq. 6}$$

The signal S may then be displayed to identify the location of the region actually being heated, e.g., the focal zone of an ultrasound transducer, as will be appreciated by those skilled in the art. Alternatively, the signal S may be compared to the temperature shift data from the first echo to identify whether the focal zone is located within a fat structure or a water-based tissue structure.

The pulse sequence may be calibrated to give roughly the same signal change for muscle Dm as for fat Df so that a rough estimate of the temperature rise may be derived. If it is known that the area wherein temperature estimates are being derived is substantially all muscle, the phase difference alone may give a more accurate result.

In the pulse sequence, the receive bandwidth for the first echo may be substantially higher than for the second echo. This results in a pulse sequence that is not much longer in time than previous single echo sequences used for phase shift temperature maps in muscle. By increasing the bandwidth during reception of the first echo, e.g., 16–32 kHz, the chemical shift artifacts from fat may be reduced. A lower bandwidth during reception of the second echo may increase the signal-to-noise ratio from the water-based signal.

In addition, fat and water-based tissues have slightly different resonant frequencies that may affect the choice of the RF excitation frequency. Because only one RF excitation pulse is used for both echoes, it is preferred to select the center frequency corresponding to the resonant frequency for water. This choice may have little effect on the first echo time used for fat, because of the relatively short echo time used in the first echo.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. A method for thermal magnetic resonance imaging, comprising:
    generating a first two echo sequence before heating a tissue region within a patient, the first two echo sequence having a first echo optimized for temperature contrast from fat tissue and a second echo optimized for temperature contrast from water-based tissue;
    heating the tissue region;
    generating a second two echo sequence after heating the tissue region, the second two echo sequence having a third echo optimized for temperature contrast from fat tissue and a fourth echo optimized for temperature contrast from water-based tissue;
    comparing the first echo to the third echo to obtain a temperature shift in fat tissue; and
    comparing the second echo to the fourth echo to obtain a temperature shift in water-based tissue.

2. The method of claim 1, wherein the step of comparing the first echo to the third echo comprises:
    measuring a magnitude difference between the third echo and the first echo; and
    correlating the magnitude difference to the temperature shift in fat tissue.

3. The method of claim 1, wherein the step of comparing the second echo to the fourth echo comprises:
    measuring a phase difference between the fourth echo and the second echo; and
    correlating the phase difference to the temperature shift in water-based tissue.

4. The method of claim 1, further comprising generating a thermal image of the tissue region based upon the temperature shifts in fat and water-based tissue.

5. The method of claim 1, wherein the step of generating a first two echo sequence comprises using a gradient echo sequence to generate the first and second echoes.

6. The method of claim 1, wherein the step of generating a second two echo sequence comprises using a gradient echo sequence to generate the third and fourth echoes.

7. The method of claim 1, wherein the step of generating a first two echo sequence comprises generating a single radio frequency (RF) excitation pulse to generate both the first echo and the second echo.

8. The method of claim 7, wherein the RF excitation pulse is configured for generating a low angle flip of less than about ninety degrees.

9. The method of claim 1, further comprising focusing ultrasonic energy towards the tissue region between the steps of generating the first and second two echo sequences.

10. A method for thermal magnetic resonance imaging, comprising:
    generating a first two echo sequence before heating a tissue region within a patient, the first two echo sequence having a first echo optimized for temperature contrast from fat tissue and a second echo optimized for temperature contrast from water-based tissue;
    directing thermal energy towards the tissue region;
    generating a second two echo sequence after directing the thermal energy towards the tissue region, the second two echo sequence having a third echo optimized for temperature contrast from fat tissue and a fourth echo optimized for temperature contrast from water-based tissue;
    comparing the third echo and the first echo to obtain a first difference;
    comparing the fourth echo and the second echo to obtain a second difference; and
    combining a complex difference between the first difference and the second difference to identify a location of the thermal energy.

11. The method of claim 10, further comprising comparing the complex difference with at least one of the first difference and the second difference to identify whether the location of the thermal energy is within fat tissue or muscle tissue.

12. The method of claim 10, wherein the first difference comprises a magnitude difference between the third echo and the first echo.

13. The method of claim 12, further comprising correlating the magnitude difference to a temperature shift in fat tissue.

14. The method of claim 10, wherein the second difference comprises a phase difference between the fourth echo and the second echo.

15. The method of claim 14, further comprising correlating the phase difference to a temperature shift in water-based tissue.

16. A method for thermal magnetic resonance imaging, comprising:
    applying a first two echo gradient echo sequence to a tissue region of a patient, the first two echo sequence generating a first echo and a subsequent second echo within the tissue region;
    directing thermal energy towards the tissue region;

applying a second two echo gradient echo sequence after directing the thermal energy towards the tissue region, the second two echo sequence generating a third echo and a subsequent fourth echo within the tissue region;

comparing the first echo to the third echo to obtain temperature shift data attributable substantially to fat tissue within the tissue region; and comparing the second echo to the fourth echo to obtain temperature shift data attributable substantially to water-based tissue within the tissue region.

17. The method of claim 16, wherein the step of comparing the first echo to the third echo comprises:

measuring a magnitude difference between the third echo and the first echo; and correlating the magnitude difference to the temperature shift for fat tissue.

18. The method of claim 16, wherein the step of comparing the second echo to the fourth echo comprises:

measuring a phase difference between the fourth echo and the second echo; and correlating the phase difference to the temperature shift for water-based tissue.

19. The method of claim 16, further comprising generating a thermal image of the tissue region based upon the temperature shift data for both fat and water-based tissue.

20. The method of claim 16, further comprising combining a complex difference between the temperature shift data for the fat tissue and the water-based tissue to identify a location of the thermal energy.

* * * * *